(12) United States Patent
Powers et al.

(10) Patent No.: US 9,714,878 B2
(45) Date of Patent: Jul. 25, 2017

(54) PRESSURE SENSITIVE DEVICE FOR FLOW DETECTION

(71) Applicant: ARROW ELECTRONICS, INC., Englewood, CO (US)

(72) Inventors: Nicholas Powers, Englewood, CO (US); Christian Curtis, Englewood, CO (US)

(73) Assignee: ARROW ELECTRONICS, INC., Englewood, CO (US)

( * ) Notice: Subject to any disclaimer, the term of this patent is extended or adjusted under 35 U.S.C. 154(b) by 476 days.

(21) Appl. No.: 14/025,376

(22) Filed: Sep. 12, 2013

(65) Prior Publication Data

US 2015/0068523 A1    Mar. 12, 2015

(51) Int. Cl.

| | |
|---|---|
| *A61M 15/00* | (2006.01) |
| *G01L 7/08* | (2006.01) |
| *A61M 15/06* | (2006.01) |
| *A61M 11/04* | (2006.01) |
| *A24F 47/00* | (2006.01) |
| *A61M 16/00* | (2006.01) |
| *H01H 35/34* | (2006.01) |

(52) U.S. Cl.
CPC .............. *G01L 7/08* (2013.01); *A24F 47/008* (2013.01); *A61M 11/042* (2014.02); *A61M 15/06* (2013.01); *A61M 2016/0024* (2013.01); *A61M 2205/8206* (2013.01); *A61M 2207/00* (2013.01); *H01H 35/346* (2013.01); *Y10T 29/49155* (2015.01)

(58) Field of Classification Search
CPC . G01L 11/08; G01L 1/086; G01L 1/16; G01L 7/08; G01L 13/025; G01L 9/0055; G01L 9/0042; A24F 47/008; A24F 7/002; A61M 11/042; A61M 15/06; A61M 2016/0024; A61M 2207/00; A61M 2205/8206; Y10T 29/49155; H01H 35/346; G01F 1/383; G01K 13/02

USPC .................................. 73/721, 861.47; 338/4
See application file for complete search history.

(56) References Cited

U.S. PATENT DOCUMENTS 3,267,233 A  *  8/1966  Basile .................. H01H 35/346
                                                200/83 N
4,288,835 A  *  9/1981  Lee ....................... G01L 9/0086
                                                361/272

(Continued)

*Primary Examiner* — Bradley Philips
*Assistant Examiner* — Victoria Leszczak
(74) *Attorney, Agent, or Firm* — Tutunjian & Bitetto, P.C.

(57) ABSTRACT

A pressure sensitive device includes a ring having a central axis, first side and second side. The ring includes a dielectric portion parallel to the central axis and between the first and second sides. A flexible membrane is connected to a periphery of the ring on the first side, the flexible membrane including a conductive portion. A perforated membrane is connected to a periphery of the ring on the second side. The perforated membrane is spaced apart and electrically isolated from the flexible membrane by the ring below a threshold pressure differential across the pressure sensitive device. The perforated membrane includes an opening therethrough and a conductive portion facing and corresponding to the conductive portion of the flexible membrane such that a threshold pressure differential across the pressure sensitive device causes deflection between the conductive portions of the flexible membrane and the perforated membrane to change an electrical property.

20 Claims, 7 Drawing Sheets

(56) References Cited

U.S. PATENT DOCUMENTS

| | | | | |
|---|---|---|---|---|
| 4,514,604 A | * | 4/1985 | Gmeinder | H01H 35/34 200/83 N |
| 8,499,766 B1 | * | 8/2013 | Newton | A24F 47/008 131/273 |
| 2007/0074734 A1 | * | 4/2007 | Braunshteyn | A24F 13/00 131/328 |
| 2008/0092912 A1 | * | 4/2008 | Robinson | A24F 47/008 131/200 |

* cited by examiner

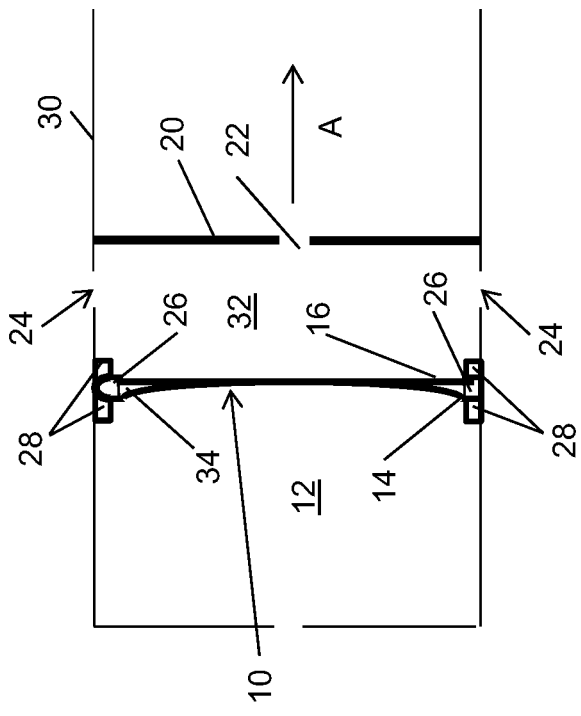
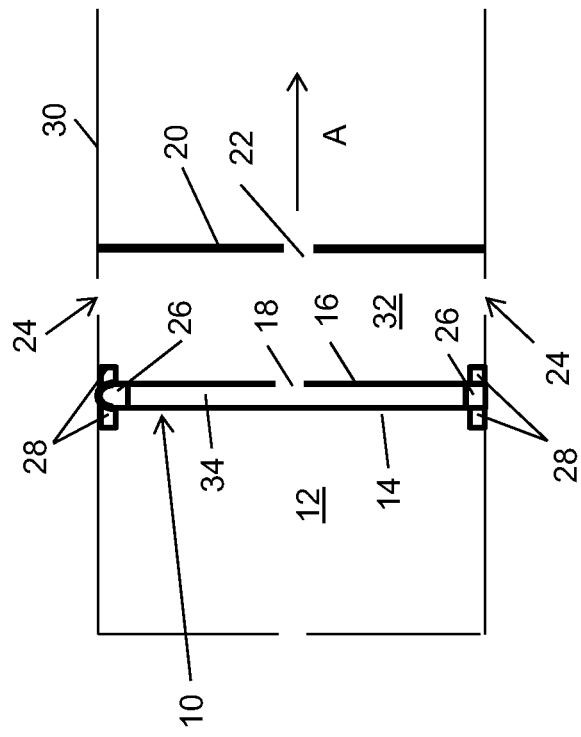

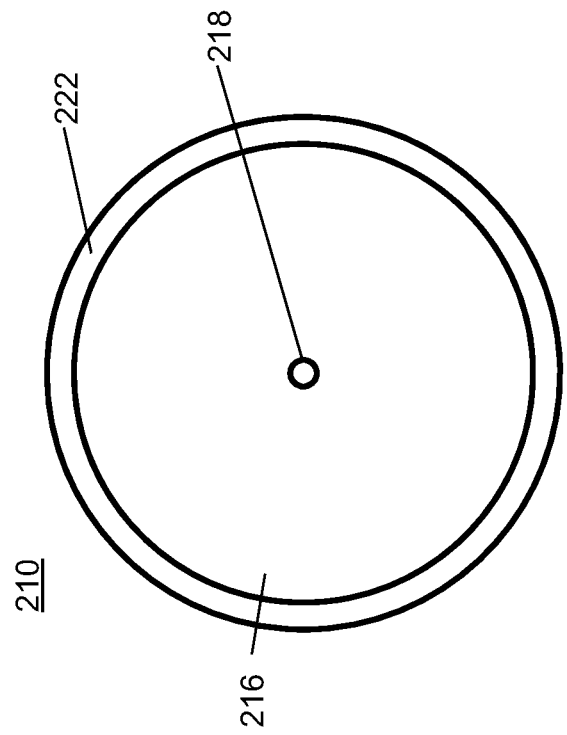
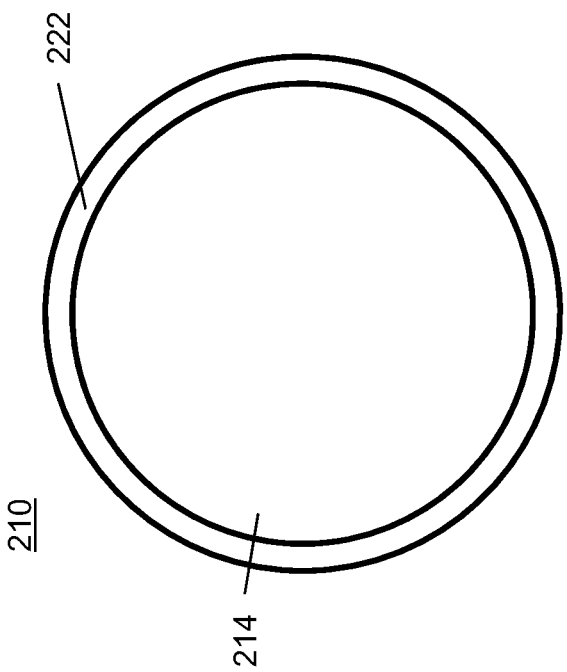

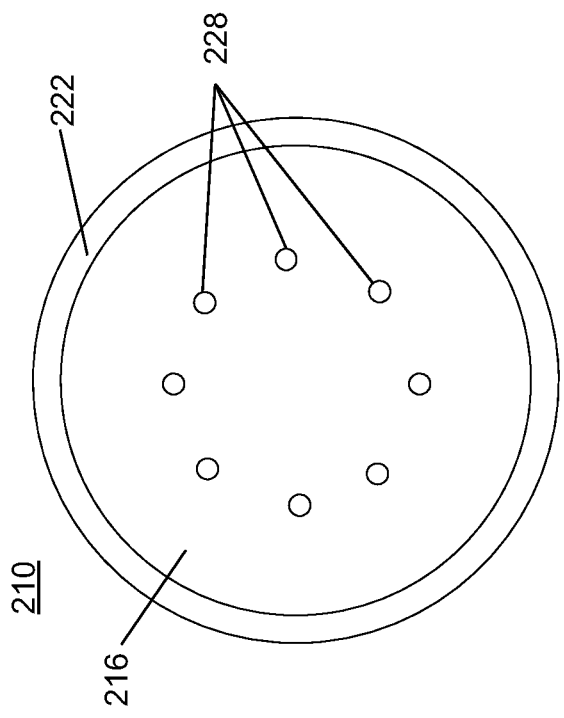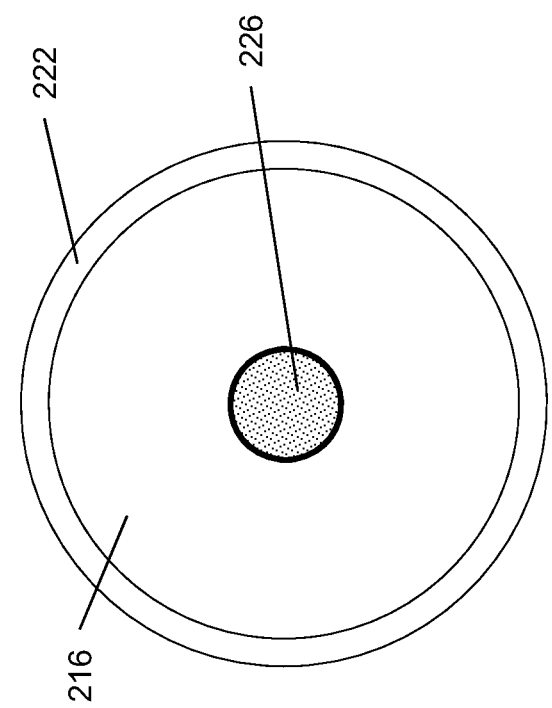

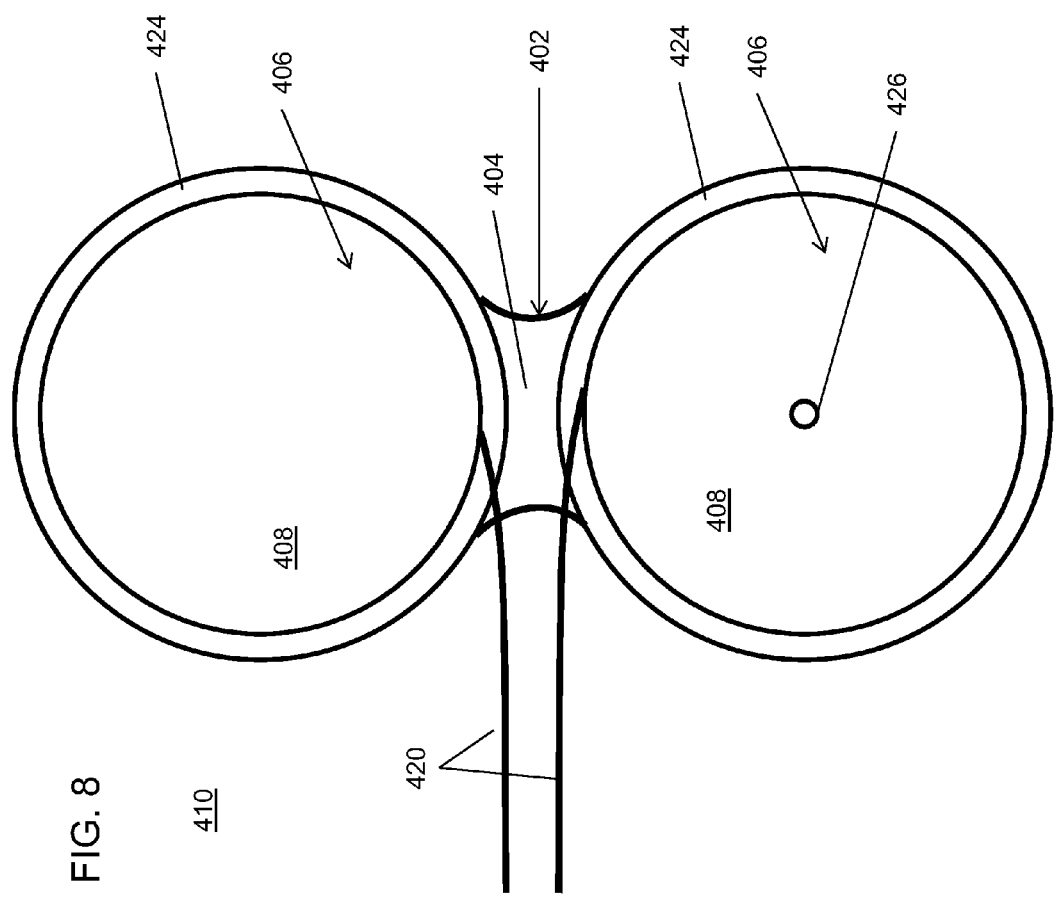

PRESSURE SENSITIVE DEVICE FOR FLOW DETECTION

BACKGROUND

Technical Field

The present invention relates to pressure sensors, and more particularly to a pressure sensitive device that deforms to change an electrical property in the presence of a pressure differential.

Description of the Related Art

Pressure sensors measure fluid pressure. A pressure sensor usually acts as a transducer that transmits an electrical signal as a function of the pressure imposed. Pressure sensors are employed for control and monitoring in many applications. Pressure sensors can also be used to indirectly measure other variables such as fluid/gas flow, speed, water level, and altitude. Pressure sensors may employ different technologies, for example, piezoresistive strain gauge, capacitive, electromagnetic, piezoelectric, optical, potentiometric, etc. Many of these pressure sensors are expensive to manufacture and require signal processing or other procedures to obtain measurements.

SUMMARY

A pressure sensitive device includes a ring having a central axis, first side and second side. The ring includes a dielectric portion parallel to the central axis and between the first and second sides. A flexible membrane is connected to a periphery of the ring on the first side, the flexible membrane including a conductive portion. A perforated membrane is connected to a periphery of the ring on the second side. The perforated membrane is spaced apart and electrically isolated from the flexible membrane by the ring below a threshold pressure differential across the pressure sensitive device. The perforated membrane includes an opening therethrough and a conductive portion facing and corresponding to the conductive portion of the flexible membrane such that a threshold pressure differential across the pressure sensitive device causes deflection between the conductive portions of the flexible membrane and the perforated membrane to change an electrical property.

An electronic inhalation device includes a chamber having a material to be dispersed, and a pressure sensitive device. The pressure sensitive device includes a ring having a central axis, a first side and a second side, the ring including a dielectric portion parallel to the central axis and between the first side and the second side, a flexible membrane connected to a periphery of the ring on the first side, the flexible membrane including a conductive portion and a perforated membrane connected to a periphery of the ring on the second side, the perforated membrane being spaced apart and electrically isolated from the flexible membrane by the ring below a threshold pressure differential across the pressure sensitive device, the perforated membrane including an opening therethrough and a conductive portion facing and corresponding to the conductive portion of the flexible membrane. A circuit has an element coupled to a battery such that a threshold pressure differential across the pressure sensitive device causes deflection between the conductive portions of the flexible membrane and the perforated membrane to enable the element to dispense the material in the chamber which is drawn out of the chamber by the pressure differential.

A method for fabricating a pressure sensitive device includes forming a substrate having two membrane portions connected by a linking portion; forming an opening in one of the membrane portions; depositing conductive material on a same side on the substrate at corresponding central locations on the two membrane portions; folding the substrate over a dielectric ring and connecting the two membrane portions to opposite sides of the ring; and providing electrical connections to the conductive material on each of the two membrane portions such that a threshold pressure differential across the pressure sensitive device causes deflection between the conductive material of the two membranes to cause an electrical change in a circuit.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 1 is a cross-sectional view of a pressure sensitive device with a pressure differential across the device that is below a pressure differential threshold in accordance with the present principles;

FIG. 2 is a cross-sectional view of a pressure sensitive device with a pressure differential across the device that is above a pressure differential threshold in accordance with the present principles;

FIG. 6 is a back view of a pressure sensitive device showing a flexible membrane in accordance with the present principles;

FIG. 7A is a front view of a pressure sensitive device showing a perforated membrane in accordance with the present principles;

FIG. 7B is a front view of a pressure sensitive device showing a porous perforated membrane in accordance with the present principles;

FIG. 7C is a front view of a pressure sensitive device showing a perforated membrane with a hole pattern in accordance with the present principles;

FIG. 8 is a top view of a pressure sensitive device showing two membrane portions or lobes connected by linking material on a same substrate and showing a ring material formed on both membrane portions in accordance with the present principles.

DETAILED DESCRIPTION OF PREFERRED EMBODIMENTS

Figure 3:
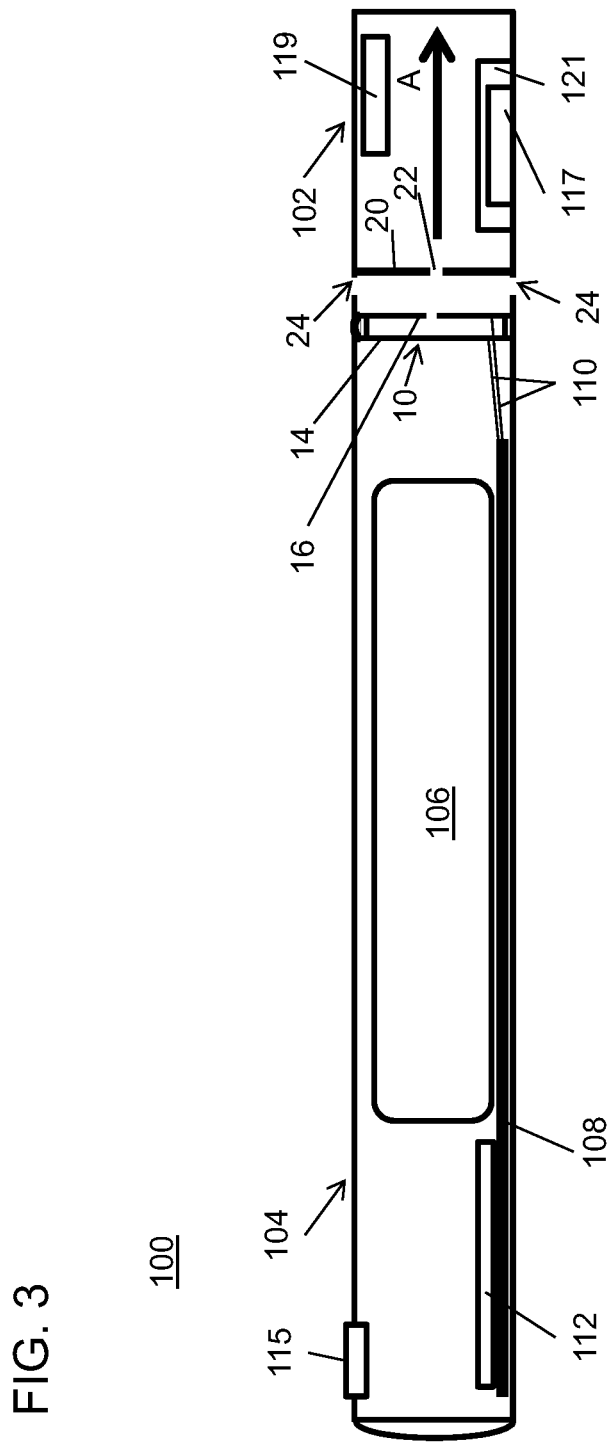
FIG. 3 is a cross-sectional view of a pressure sensitive device employed in an inhalation system with a pressure differential across the device that is below a pressure differential threshold in accordance with the present principles.

In accordance with the present principles, a pressure sensitive device is employed to detect the presence of a pressure differential created due to fluid flow. The pressure sensitive device includes components configured to react to a particular pressure differential to provide a pressure switch. When fluid flow causes a sufficient pressure differential between the two sides of the pressure sensitive device, at least one of the sides deflects or distorts to cause an electrical change such as electrical contact or a capacitive change between two surfaces allowing a signal to be transmitted between the two sides.

In one embodiment, the pressure sensitive device sensor utilizes two conductive pads on a flexible substrate that are separated by a very small gap dependent on a pressure to be sensed. There are lead wires coupled to each conductive side to permit a signal to pass through when the two conductive sides are in contact with one another. A hole is present in on one conductive side to permit the two sides to contact and not form a pressure between the two conductive sides.

In another embodiment, the pressure sensitive device utilizes a captive sensing scheme between two conductive pads that are separated by a very small gap dependent on a pressure to be sensed. There are lead wires coupled to each conductive side. When the gap between the two conductive sides decreases and a capacitance threshold is met, a signal is transmitted. A hole is present in on one conductive side to permit the two sides to contact and not form a pressure between the two conductive sides.

Most conventional devices measure changes in a material as it distorts due to air pressure. The present principles employ material distortion to a point where the materials come into contact (or come closer together) to function as a simple switch or a variable capacitor. This present implementation is much simpler from a sensing perspective and a manufacturing perspective providing simple functionality. Also, the present principles use little or no standby power which results in significant power savings especially for portable or limited power systems.

It is to be understood that the present invention will be described in terms of a given illustrative structure having a pressure sensitive device disposed in an air-flow tube; however, other architectures, structures, materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, an illustrative embodiment for a pressure sensitive device 10 is shown in accordance with the present principles. The pressure sensitive device 10 includes a first conductive membrane 14 stretched or disposed across a chamber 12. The chamber 12 may be pressurized or may include a fluid inlet through its walls to maintain a pressure (e.g., ambient pressure). The membrane 14 includes a conductive material at least on a side facing a perforated membrane 16. Perforated membrane 16 also includes a conductive material at least on a side facing membrane 14. The membrane 14 and perforated membrane 16 are supported on a ring 26 that follows an interior surface of the chamber 12. The ring 26 may include an insulator material although any material or combinations of materials may be employed for the ring 26 as long as the membrane 14 and perforated membrane 16 are electrically isolated in their initial positions as depicted in FIG. 1.

While many configurations may be employed to secure the device 10 in the chamber 12, detents 28 are illustratively provided to prevent movement of the device 10 during pressure changes. Other configurations may include adhesive, grooves, an o-ring seal, a gasket seal, etc.

A hollow tube 30, which is preferably rigid enough to sustain a differential between its interior and exterior, includes a partition 20 formed therein. The partition 20 includes an opening 22 therein to permit fluid to be drawn from a region 32. The opening 22 in partition 20 functions as a focusing gasket which concentrates airflow onto the sensor device 10 to increase sensitivity. In some embodiments, a focusing gasket or other device may be employed on either side of the device 10 to direct flow against a central portion of the membrane 14 to increase sensitivity.

When fluid, such as air, water, etc. is drawn through the opening 22 in the direction of arrow "A", the fluid is replenished through openings 24. The opening 22 and openings 24 have cross-sectional areas and other flow constraints configured such that drawing fluid through the opening 22 causes an instantaneous pressure drop in region 32. This pressure drop is transmitted to a region 34 between the membrane 14 and perforated membrane 16 through a perforation 18 in the perforated membrane 16. The perforation 18 prevents pressure buildup between the membrane 14 and perforated membrane 16. It should be understood that the perforated membrane 16 may include a rigid or semi-rigid material (less flexible) to stabilize the outer ring 26 to prevent flexing of the entire sensor device 10 and concentrating flexure of the membrane 14 at a central portion of the membrane 14.

Referring to FIG. 2, the pressure drop in region 32 causes the membrane 14 to deform in the direction of the pressure drop (arrow "A"). The membrane 14 and perforated membrane 16 have a thickness and are spaced apart to permit contact between the membrane 14 and the perforated membrane 16 when a threshold pressure drop has been reached. In an alternate embodiment, contact is not needed between the membranes 14, 16 as a capacitance may be monitored therebetween to determine when a threshold distance between the membranes 14, 16 is achieved.

Contact between membrane 14 and perforated membrane 16 create a closed switch to provide an electrical connection. The thickness of the membrane 14 and a distance between the membrane 14 and the perforated membrane 16 may be designed to provide different threshold pressure drops at which contact (or distance) between membranes 14 and 16 is made.

Referring to FIG. 3, in a particularly useful embodiment, an electronic inhalation device 100, e.g., an electronic cigarette, an electronic medical inhaler, a treatment for breath order, etc., includes the pressure sensitive device 10. The pressure sensitive device 10 includes leads or wires 110 that are electrically connected to a printed circuit board (PCB) 108 or other circuit. The PCB 108 is powered by a battery 106 or other energy storage device. When a user draws air from a proximal end portion 102 of the inhalation device 100, the device 10 is caused to make contact (or close a distance) between the membranes 14 and 16, which completes a circuit through the wires 110 on the PCB 108 or adjusts a capacitance. The battery 106 may be rechargeable and the device 100 may include recharging circuits and ports (e.g., a USB port) to enable recharging.

In one embodiment, when a circuit is completed by contact between membranes 14 and 16, power is drawn from the battery 106 to perform a function. The function may include lighting a diode or other light source 115, heating an element 117 on the PCB 108 or connected to the PCB 108 to vaporize a liquid in a substrate or container 121, release a substance from a chamber by a dispersion mechanism 119, etc. In one embodiment, a microcontroller 112 may be employed to measure pressure differential (capacitance or whether contact has been made). When a threshold pressure is achieved due to airflow, the microcontroller 112 can send a signal to perform a function or functions. In one example, the microcontroller enables engages the heating element 117 or dispersion mechanism 119. In the present example, the energy from the battery 106 vaporizes a liquid to be inhaled by a user. Other arrangements and configurations are also contemplated. For example, the membranes 14 and 16 may be permeable or semi-permeable (e.g., fabric membranes or portions thereof) or include permeable portions to permit fluid flow through the membranes 14 and 16.

The proximal end portion 102 may or may not include electrical devices (e.g., element 117). The proximal end portion 102 may be removable (by a threaded connection, bayonet connection, snap-on connection etc.) to enable reuse of the battery 106, PCB 108, microcontroller 112, device 10, etc. In this want the distal end portion 104 can be reused for different medications, different flavors, multiple uses, etc. The present embodiments are simple, low cost and use little or no standby power. The design is durable and easily scalable to different applications and capacities.

Figures 4A, 4B, 5:
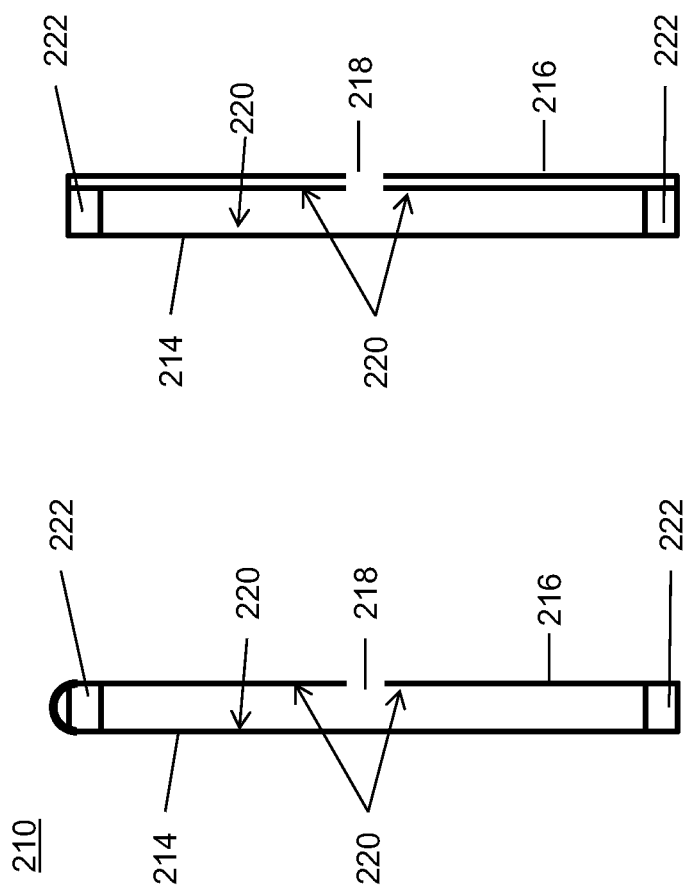
FIG. 4A is a cross-sectional view of a pressure sensitive device having a single substrate material for both membranes in accordance with the present principles.
FIG. 4B is a cross-sectional view of a pressure sensitive device having a rigid or printed circuit board for one of the membranes in accordance with the present principles.
FIG. 5 is a cross-sectional view of the pressure sensitive device with a rigid curved membrane in accordance with the present principles.

Referring to FIG. 4A, a pressure sensitive device 210 is shown in accordance with another embodiment. The pressure sensitive device 210 includes a flexible membrane 214 and a flexible or rigid membrane 216, which has a small diameter hole 218 or other opening at approximately its center to prevent pressure buildup between the membranes 214 and 216. The two membranes 214 and 216 may be connected or built on a same substrate or as a single sheet and folded over to provide ease manufacturing and reduce cost.

Only surfaces 220 need to be conductive, therefore, a base material for membranes 214 and 216 may be a non-conductive material (e.g., a polymer), and the surfaces may be plated, inked, painted, deposited or otherwise surfaced with conductive material. Conductive surfaces 220 may be mounted or applied on the membranes 214, 216 by, e.g., employing a conductive ink or paint instead of a distinct separate material (e.g., a foil); though a distinct separate material may be employed. Material choices for the conductive surfaces 220 may include copper, silver, gold, aluminum, conductive polymers, conductive inks, carbon ink, silver chloride, other inks, paints, etc.

In one embodiment, the two membranes 214 and 216 include a same base or substrate material and are wrapped around a ring 222. Alternately, the two membranes 214 and 216 are separated and attached to the ring 222. The ring 222 is provided between the two membranes 214, 216 to form a gap 224 which maintains the membranes 214 and 216 apart a predetermined amount and helps to minimize false positives (e.g., erroneously triggering the pressure switch). The material for the ring 222 may include any non-conductive material (e.g., plastic, paper, cardboard, foam, sponge, silicon, etc.) or non-conductive layers or coating on a conductive material (e.g., a plastic coated metal ring). In one embodiment, the membranes 214, 216 include conductive materials and the ring 222 includes non-conductive material.

In another embodiment, the ring 222 and the base or substrate material of the membranes 214, 216 are integrally formed from a same material. The flexible substrate forming the membranes 214, 216 may have a ring 222 molded therein or printed thereon. This integration would result in a lower part count and a simpler system.

Referring to FIG. 4B, the membrane 216 may include a rigid material (conductive or non-conductive) to provide support for the device 210 and assist in its mounting in a tube or the like. In one embodiment, the membrane 216 may include a PCB (216) in contact with the ring 222 or spacer. The membrane 214 includes a flexible material resulting in a pressure sensor which when the flexible material 214 deflects, the PCB (216) is engaged to form an electrical connection or capacitance is altered therebetween.

Referring to FIG. 5, a pressure sensitive device 310 is shown in accordance with another embodiment. The pressure sensitive device 310 includes a flexible membrane 314 and a rigid curved membrane or sheet 316, which includes a small diameter hole 318 at approximately its center to prevent pressure buildup between the membrane 314 and curved membrane 316. Other shapes are also contemplated. The two membranes 314 and 316 may be connected or built on a same substrate or as a single sheet and folded over to provide ease manufacturing and to reduce cost. Only surfaces 220 need to be conductive, therefore, a base material for membranes 314 and 316 may be a non-conductive material (e.g., a polymer), and the surfaces may be plated, inked, painted, deposited or otherwise surfaced with conductive material.

It should be understood that in the described embodiments, the flexible membrane 14, 114, 214, 314, etc. may be pulled by vacuum or pushed by a higher back pressure.

Referring to FIG. 6, a back view of the pressure sensitive device 210 shows the membrane 214 coupled to the ring 222. The device 210 is illustratively depicted as a circular cross-section; however, any shaped cross-section may be employed, e.g., polygonal, oval, triangle, etc. Connection to the ring 222 by membrane 214 may be provided using adhesive, integral formation (molding, printing, etc.), heat sealing or by other mechanical connection.

Referring to FIG. 7A, a front view of the pressure sensitive device 210 shows the membrane 216 coupled to the ring 222. The device 210 is illustratively depicted as a circular cross-section; however, any shaped cross-section may be employed, e.g., polygonal, oval, triangle, etc. Connection to the ring 222 by membrane 216 may be provided using adhesive, integral formation (molding, printing, etc.), heat sealing or by other mechanical connection.

In this embodiment, the membrane 216 includes a single hole 218 in a center of the membrane 216. While a single hole 218 is depicted, a plurality of holes or hole patterns may be employed. For example, as depicted in FIG. 7B, a pattern of micro holes 226 may be provided through the membrane 216 to permit pressure to dissipate between diaphragm portions (membranes 214, 216) but to also limit the amount of material flowing between the sensor pads to limit contamination and increase lifetime of the sensor device 210.

In other embodiments, a circle pattern of holes 228 may be employed as depicted in FIG. 7C. Other patterns or hole arrangements may also be employed. In one embodiment, holes may be provided through both membranes 214 and 216 with different hole arrangements to provide electrical contact between the membranes 214 and 216 when fluid is drawn through the sensor device 210 at a particular threshold rate (e.g., a sufficient pressure differential is supplied to cause contact).

The hole diameters and the ring width can be increased or decreased based on the application. Changing of these dimensions and other factors will affect the pressure sensitivity.

Referring to FIG. 8, a manufacturing arrangement for fabricating a pressure sensitive device 410 is shown in accordance with one illustrative embodiment. A flexible substrate 402 includes linking material 404 and two lobes 406. The two lobes 406 are the substrate or base material and have a conductive material 408 formed thereon (but not on the linking material 404). The conductive material 408 may be deposited metal, conductive paint or ink, etc. A spacer 424 may be molded onto or formed integrally with the substrate 402. In one embodiment, the linking material 404 between the two lobes 406 may be folded to permit the spacer 424 on each lobe 406 to coincide such that the conductive surfaces 408 face one another. Wire leads 420 connect to the conductive material 408. The wire leads 420 may be soldered to the conductive material 408 or may be conductive epoxied, mechanically coupled or otherwise electrically coupled to the conductive material 408 so that an electrical signal can be passed into and/or through the sensor under threshold pressure conditions.

In accordance with the present principles, several illustrative embodiments have been described that are capable of sensing airflow (or other fluid flow) for extremely low cost with easily producible materials. Some advantages include ease of implementation, low cost, robustness, low power dissipation and ease of manufacturing.

Figure 9:
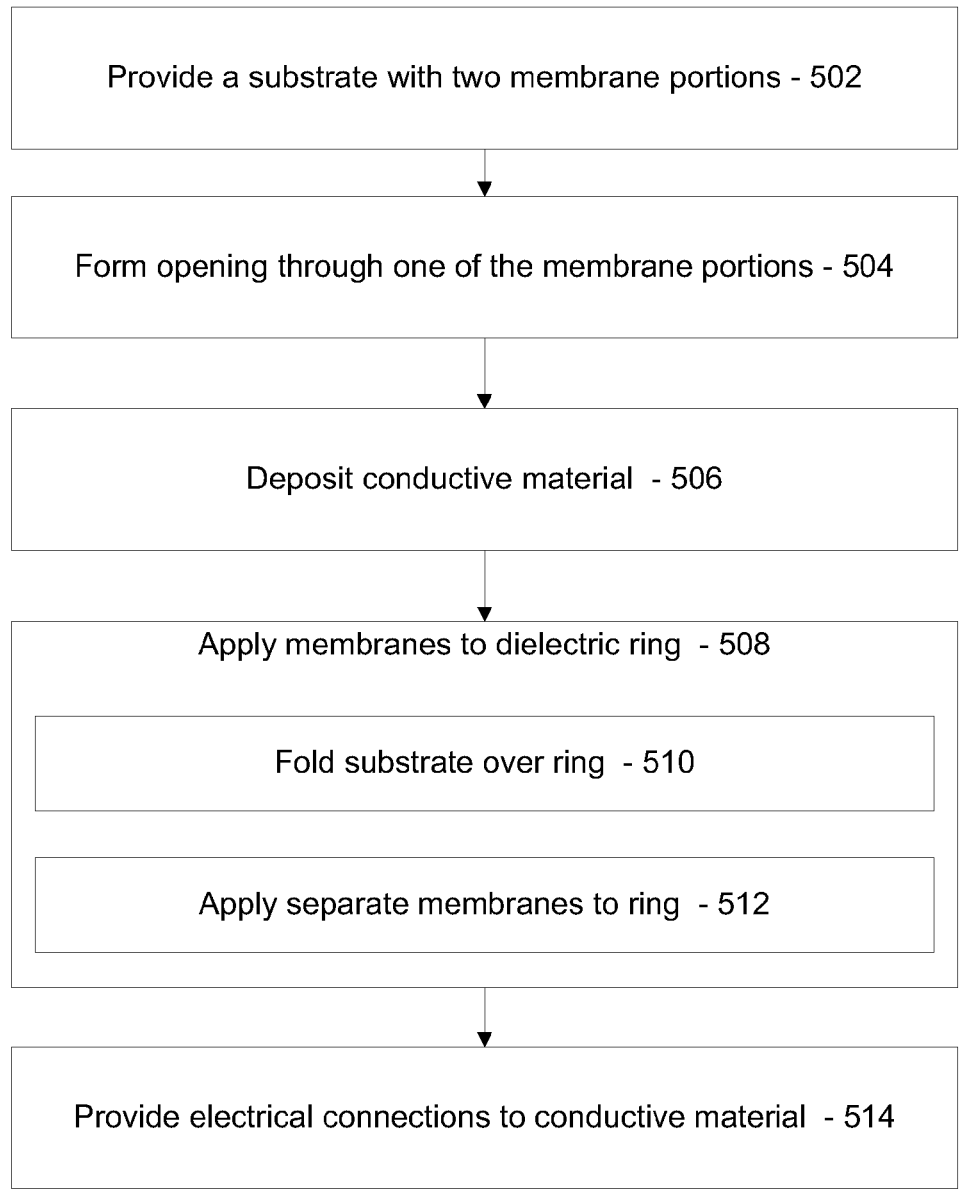
FIG. 9 is a block/flow diagram showing a method for fabrication of the pressure sensitive device in accordance with one illustrative embodiment.

Referring to FIG. 9, a method for fabricating a pressure sensitive device is shown in accordance with illustrative embodiments. It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In block 502, a substrate is provided having two membrane portions connected by a linking portion. The substrate may be stamped from an extruded sheet, molded or otherwise formed from a polymeric or other dielectric material. In block 504, an opening is formed in one of the membrane portions. This opening may include a pattern of holes or a single hole. The opening may formed by stamping, during molding or by other processes. An additional material may be added on or over the hole or holes in the membrane portion (a micropore sheet, etc.) at a later time.

In block 506, conductive material is deposited on a same side on the substrate at corresponding central locations on the two membrane portions. This may include a metal deposition by e.g., sputtering, chemical vapor deposition (CVD), etc. or by painting or printing (with conductive paint or ink), etc.

In block 508, the two membrane portions are applied to a dielectric ring. The dielectric ring may be formed by depositing, molding or inking a dielectric material on at least one of the two membrane portions or portions of the dielectric ring may be formed on both of the two membrane portions.

In block 510, the two membrane portions may be applied to the dielectric ring by folding the substrate over the dielectric ring and connecting the two membrane portions to opposite sides of the ring. In another embodiment, the two membrane portions may be separated and added to opposite sides of the ring, in block 512.

In block 514, electrical connections are provided to the conductive material on each of the two membrane portions. This may include soldering, conductive epoxy, mechanical connections (e.g., crimping, cold welding, etc.). The device is formed such that a threshold pressure differential across the pressure sensitive device causes deflection and/or contact between the conductive materials of the two membranes to change an electrical property of a circuit.

Having described preferred embodiments for a pressure sensitive device for flow detection (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A pressure sensitive device, comprising:
    a hollow tube having a longitudinal axis and configured to permit air suction through one end portion of the tube;
    a ring fixedly mounted in the tube and having a central axis, a first side and a second side, the ring including a dielectric portion parallel to the central axis and between the first side and the second side;
    a flexible membrane disposed in the tube and mounted directly on a periphery of the ring on the first side, the flexible membrane including a conductive portion; and a perforated membrane disposed in the tube and connected to a periphery of the ring on the second side, the second side being closer to the one end portion that permits air suction therethrough relative to the first side, the perforated membrane being spaced apart and electrically isolated from the flexible membrane by the ring below a threshold pressure differential across the pressure sensitive device within the tube, the perforated membrane including an opening therethrough and a conductive portion facing and corresponding to the conductive portion of the flexible membrane such that a threshold pressure differential along the longitudinal direction of the tube across the pressure sensitive device causes the flexible membrane to be drawn into the perforated membrane by the suction such that deflection between the conductive portions of the flexible membrane and the perforated membrane along the longitudinal direction of the tube changes an electrical property.

2. The device as recited in claim 1, wherein the flexible membrane includes a polymeric material and the conductive portion on the flexible membrane includes one of conductive paint, conductive ink and deposited metal.

3. The device as recited in claim 1, wherein the perforated membrane includes a rigid material.

4. The device as recited in claim 1, wherein the ring includes one of a dielectric ring and a dielectric coating on a conductive material.

5. The device as recited in claim 1, further comprising a focusing gasket mounted in the tube and spaced apart from the pressure sensitive device along the longitudinal direction of the tube.

6. The device as recited in claim 1, wherein the flexible membrane and the perforated membrane are integrally formed from a same substrate.

7. The device as recited in claim 1, wherein the ring is formed by deposition on at least one of the flexible membrane and the perforated membrane.

8. The device as recited in claim 1, wherein the perforated membrane includes a printed circuit board.

9. An electronic inhalation device, comprising:
a chamber having a material to be dispersed;
a pressure sensitive device mounted within a hollow tube having a longitudinal axis and configured to permit air suction through one end portion of the tube, the pressure sensitive device including:
a ring fixedly mounted in the tube and having a central axis, a first side and a second side, the ring including a dielectric portion parallel to the central axis and between the first side and the second side;
a flexible membrane disposed in the tube and mounted directly on a periphery of the ring on the first side, the flexible membrane including a conductive portion; and
a perforated membrane disposed in the tube and connected to a periphery of the ring on the second side, the second side being closer to the one end portion that permits air suction therethrough relative to the first side, the perforated membrane being spaced apart and electrically isolated from the flexible membrane by the ring below a threshold pressure differential across the pressure sensitive device within the tube, the perforated membrane including an opening therethrough and a conductive portion facing and corresponding to the conductive portion of the flexible membrane; and
a circuit having an element coupled to a battery such that a threshold pressure differential along the longitudinal direction of the tube across the pressure sensitive device causes the flexible membrane to be drawn into the perforated membrane by the suction such that deflection between the conductive portions of the flexible membrane and the perforated membrane enables the element to dispense the material in the chamber and draw out the material from the chamber by the pressure differential.

10. The device as recited in claim 9, wherein the flexible membrane includes a polymeric material and the conductive portion on the flexible membrane includes one of conductive paint, conductive ink and deposited metal.

11. The device as recited in claim 9, wherein the perforated membrane includes a rigid material.

12. The device as recited in claim 9, wherein the ring includes one of a dielectric ring and a dielectric coating on a conductive material.

13. The device as recited in claim 9, further comprising a focusing gasket mounted in the tube and spaced apart from the pressure sensitive device along the longitudinal direction of the tube.

14. The device as recited in claim 9, wherein the flexible membrane and the perforated membrane are integrally formed from a same substrate.

15. The device as recited in claim 9, wherein the ring is formed by deposition on at least one of the flexible membrane and the perforated membrane.

16. The device as recited in claim 9, wherein the perforated membrane includes a printed circuit board and the circuit is formed on the printed circuit board.

17. The device as recited in claim 9, wherein the circuit includes a printed circuit board.

18. The device as recited in claim 1, further comprising at least one opening in the tube to permit replenishment of air in the tube.

19. The device as recited in claim 1, wherein the ring is secured within the tube about a circumference of the ring.

20. The device as recited in claim 9, further comprising at least one opening in the tube to permit replenishment of air in the tube.

* * * * *